Figure 1:
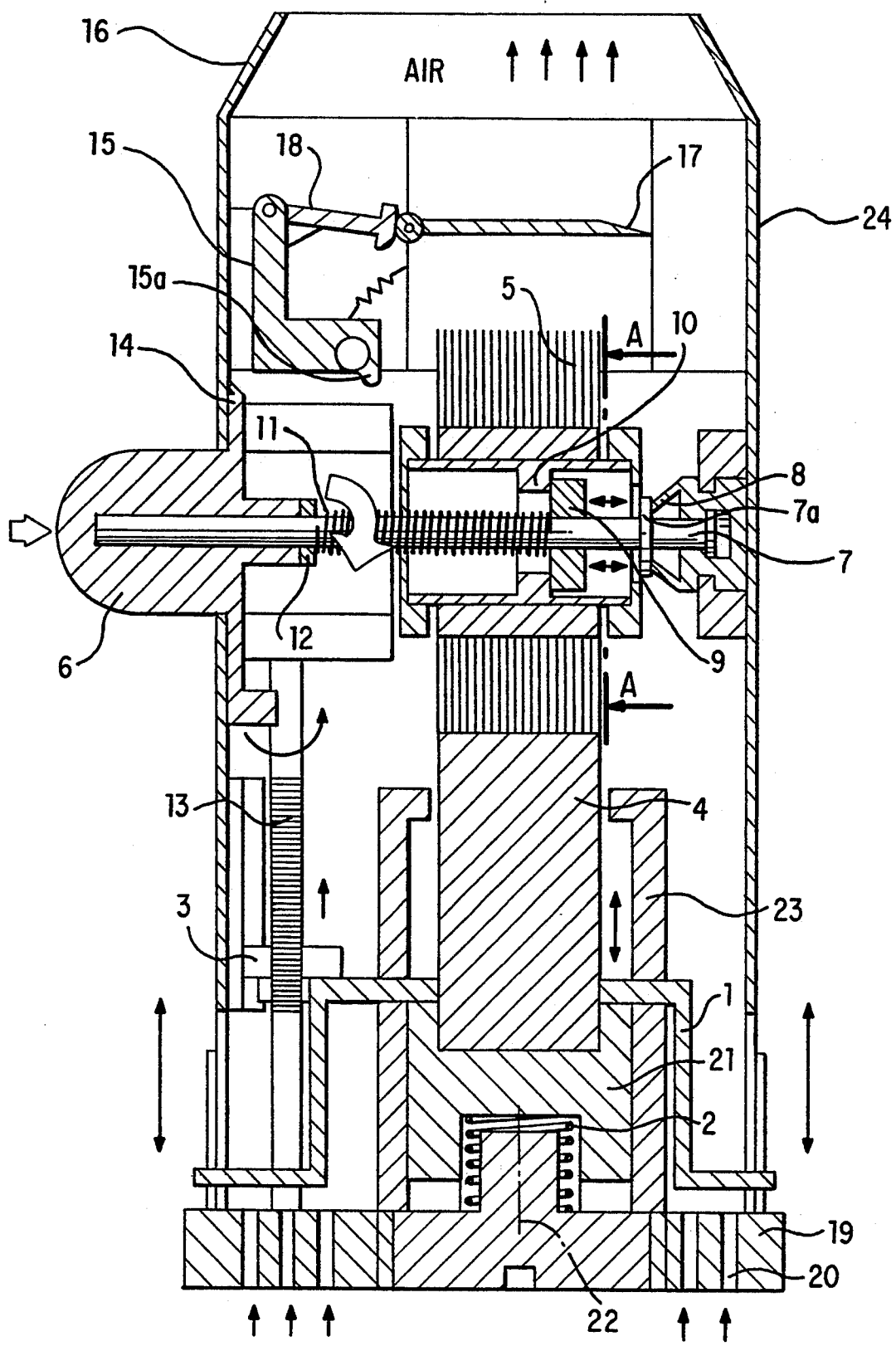

United States Patent [19]

Poss et al.

[11] Patent Number: 5,347,999
[45] Date of Patent: Sep. 20, 1994

[54] INHALATION DEVICE FREE FROM PROPELLANT GAS HAVING BRUSH ABRADING POWDER FROM TABLET

[75] Inventors: Gerhard Poss, Schriesheim; Jurgen Wittekind, Frankfurt am Main, both of Fed. Rep. of Germany

[73] Assignee: Boehringer Ingelheim KG, Ingelheim am Rhein, Fed. Rep. of Germany

[21] Appl. No.: 977,449

[22] PCT Filed: Aug. 13, 1991

[86] PCT No.: PCT/EP91/01531
§ 371 Date: Apr. 23, 1993
§ 102(e) Date: Apr. 23, 1993

[87] PCT Pub. No.: WO92/04067
PCT Pub. Date: Mar. 19, 1992

[30] Foreign Application Priority Data

Aug. 30, 1990 [DE] Fed. Rep. of Germany ....... 4027390

[51] Int. Cl.$^5$ ................... A61M 15/08; A61M 16/00; A61M 31/00; B67D 5/64
[52] U.S. Cl. ..................... 128/203.15; 128/203.21; 128/203.23; 604/57; 222/162
[58] Field of Search ............ 128/203.12, 203.13, 128/203.15, 203.19, 203.21, 203.23; 604/57-64; 222/162

[56] References Cited

U.S. PATENT DOCUMENTS

| 2,587,215 | 2/1952 | Priestly | 128/203.15 |
| 3,456,645 | 7/1969 | Brock | 128/200.23 |
| 3,921,637 | 11/1975 | Bennie et al. | 128/203.15 |
| 5,176,132 | 1/1993 | Drought et al. | 128/203.15 |

FOREIGN PATENT DOCUMENTS

| 0407028A2 | 1/1992 | European Pat. Off. |  |
| 25422 | 4/1883 | Fed. Rep. of Germany. |  |
| 332767 | 1/1920 | Fed. Rep. of Germany. |  |
| 3535561 | 5/1986 | Fed. Rep. of Germany. |  |
| 544945 | 10/1922 | France. |  |
| 615252 | 1/1927 | France | 128/203.23 |
| 1392192 | 4/1975 | United Kingdom | 128/200.14 |

Primary Examiner—Kimberly L. Asher
Attorney, Agent, or Firm—Sterne, Kessler, Goldstein & Fox

[57] ABSTRACT

The invention relates to a propellent-free inhalation device having a supply of solidified medicinal substance to be inhaled, a manually operable metering device for removing a given dose of the medicinal substance for the inhalation process and having a mouthpiece for actively breathing in and an air space for distributing the particular dose of medicinal substance in the air stream. An abrasion device, in the form of a brush comprising a plurality of bristles, is used to abrade the medicinal substance to form the dose.

19 Claims, 3 Drawing Sheets

INHALATION DEVICE FREE FROM PROPELLANT GAS HAVING BRUSH ABRADING POWDER FROM TABLET

The invention relates to an inhalation device free from propellent gas, having a supply of a medicinal substance which is to be inhaled, a manually operable metering device for removing a given dose of the medicinal substance for the particular inhalation process and with a mouthpiece for actively breathing in and an air space for distributing the particular dose of medicinal substance in the air stream.

An inhalation device of this kind is known from DE 35 35 561 A1.

In this known inhalation device, below the storage container and parallel to the mouthpiece is a rotary charging valve which has wells (metering chambers) for measuring out the medicinal substance. If the wells are turned towards the storage container they are automatically filled. If, as a result of a 180° rotation of the charging valve, the filled well is turned towards the air chamber of the mouthpiece, the dose of powder falls out of the well, as a result of gravity, with the aid of a jogging mechanism, into a cavity in the air channel and from there is inhaled into the lungs or bronchial tubes of the patient by means of active breathing in. The air channel has a constriction which is intended to promote the mixing of the air with the medicinal substance by turbulence.

This known device, like numerous other known devices, is based on the principle of storing the medicinal substance in powder form in a storage container and measuring out the dose by filling a metering chamber. The contents of the metering chamber are then expelled by gravity or with the aid of the active breathing in of the patient, possibly with a mechanical aid.

An inhalation device using this method of metering has the disadvantage that the dosage to be inhaled is not sufficiently reproducible and is not satisfactorily dispersed.

The aim of the invention is to start with a propellent-free inhalation device of the kind described hereinbefore and design it so that the dose breathed in is highly reproducible and is well dispersed.

According to the invention, this problem is solved by providing a holder in which the supply of medicinal substance, solidified in a given geometric structure, is contained, and associated with this holder, as a metering device, is an abrasion device for mechanically abrading the given dose.

Thus, in the propellent-free inhalation device according to the invention, the medicinal substance is stored not in powder form but in solid form; the required dose is only powdered immediately before the inhalation process by a mechanical operation. This mechanical operation, i.e. the abrasion of the medicinal substance, can be made relatively accurate and reproducible, so that the dose of powdered medicinal substance breathed in is also highly reproducible.

The solidified supply of medicinal substance may be prepared, for example, by mixing micronised active substance (particle size < 10 $\mu$m) with a physiologically harmless excipient or carrier, such as lactose, and compressing the mixture to form a body which has a constant cross-section in the direction of its longitudinal axis. The shape of the cross-section may otherwise take a variety of forms, with the result that the body may be, for example, a cube, cylinder or prism. To ensure that the abrasion is carried out as uniformly as possible, a device may be provided which causes the body to rotate about its longitudinal axis, possibly so that the body is rotated through 25° to 90°, e.g. 55°, on each actuation of the device.

The invention is explained more fully with reference to some embodiments by way of example shown in the drawings. Characterising features of the invention will become apparent.

Figure 2:
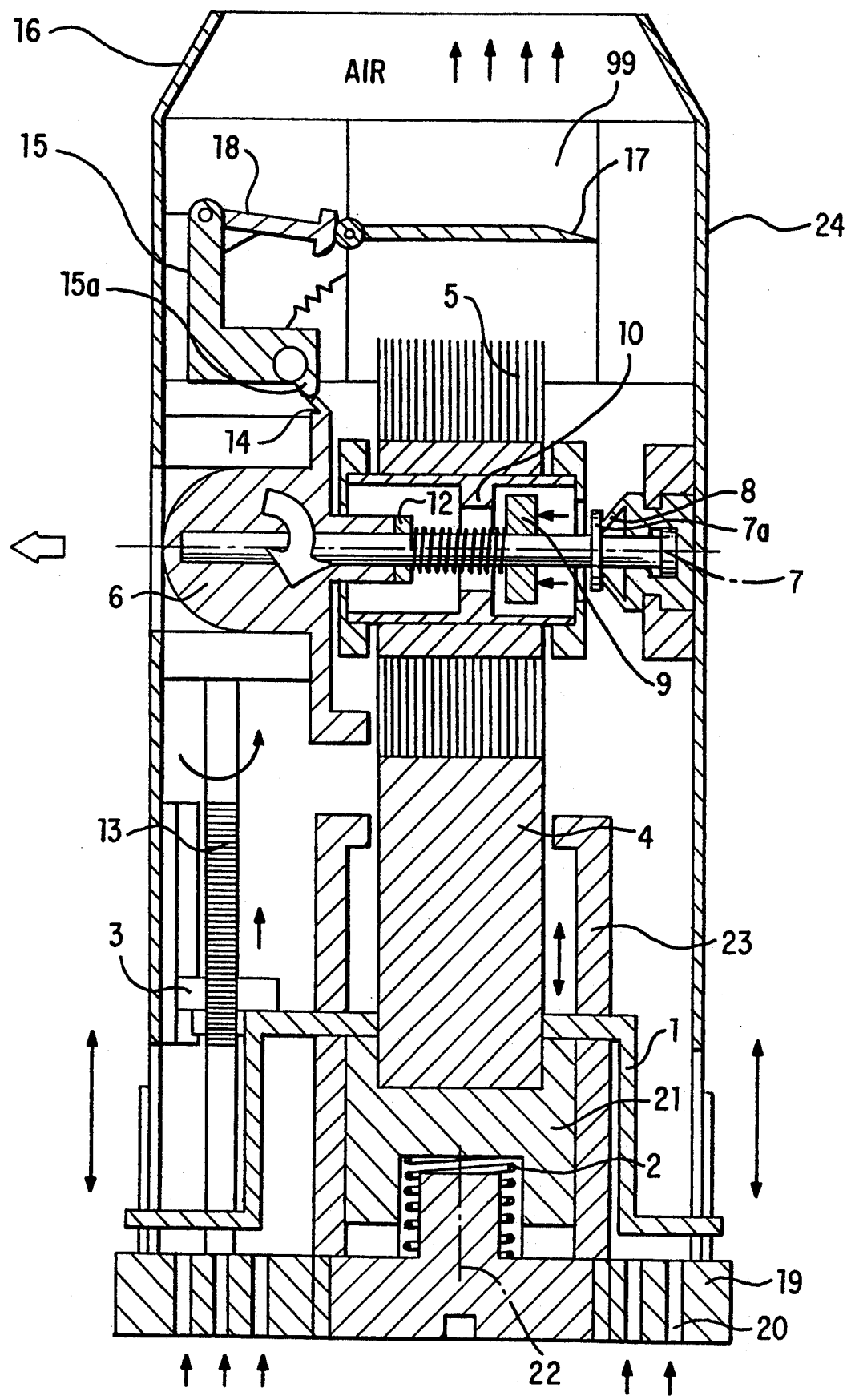
Figure 3:
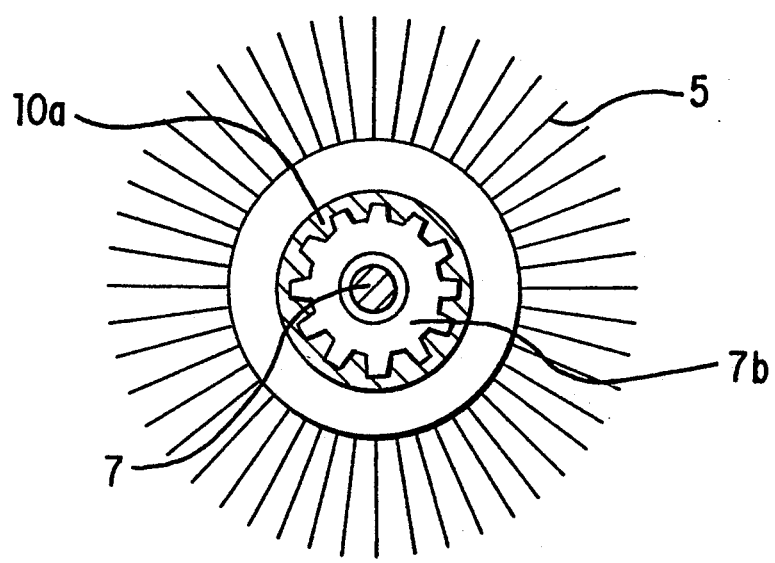

In the drawings:

FIG. 1 is an embodiment by way of example of the propellent-free inhalation device according to the invention in the unused position, FIG. 2 shows the inhalation device according to FIG. 1 in the primed position, i.e. ready for inhaling, FIG. 3 shows a section along the line A—A in FIG. 1, illustrating another embodiment.

The propellent-free inhalation device shown in FIG. 1 consists of a housing 24 which has a mouthpiece 16 at the top and is closed off at the other end by a baseplate 19 which has air inlet slots 20 and a central base portion 22 which can be unscrewed.

In the housing, in the region of the base, a tablet holder 1 is arranged in an axially movable manner and on it is fixed, in a tablet recess 21, a square tablet 4 of the medicinal substance to be measured out and inhaled. The movement of the tablet 4 is guided by means of a tablet guide 23.

The inhalation device also has a rotatable brush arrangement 5 which can be brought into contact with the tablet 4. The tablet holder 1 is held down, under the bias of a compression spring 2 which rests on the central base portion 22 and on the tablet recess 21, by means of a protective cap (not shown) which is fitted over the inhalation device. When the protective cap is removed the tablet holder 1 is pressed against a stop 3 by the compression spring and in this way the tablet 4 secured in the tablet holder 1 is pressed against the brush 5.

In the upper part of the inhalation device is a push button 6 which is associated, via a pushing member 12, with a spindle 7 running in the transverse direction. This spindle presses with the stop 7a against a plate spring 8. A friction drive-wheel 9 is fixedly connected to the spindle 7 and engages operatively with a brush drive-wheel 10 which is associated with the brush 5 and drives it. Between the push button 6 and the friction drive-wheel 9 is a spring 11.

By the actuation of the push button 6 the inhalation device is primed, i.e. brought into the state ready for operation. The arrangement of the components is such that the spindle 7 initially performs a slight movement of translation to the right towards the plate spring 8. In FIG. 1 this is indicated, at the level of the section A-A, by corresponding arrows. The friction drive-wheel 9 fixedly connected to the spindle 7 is separated from the brush friction wheel 10. As the push button 6 is pressed in further, the spring 11 is loaded and the spindle 7 performs one or more rotations, caused by a steep screw thread on the spindle and the pushing member 12 firmly connected to the push button 6.

For adjustment of the stop 3, another spindle 13 is provided, arranged parallel to the longitudinal axis of the device. This spindle is coupled to the other spindle 7 via known components in such a way that, at the same time as the push button is pressed in, the spindle 13 is rotated through a defined angle, e.g. 180°, by interlocking or frictional engagement. This causes the stop 3 to move on by a defined amount. This determines the quantity (dose) to be brushed off the tablet and ensures consistency of metering.

In order to lock the device in the primed state the push button has a resilient engaging pin 14 which can be brought into engagement with a lug 15a of a bell crank lever 15. Once the push button 6 has been pushed in fully, it is locked in position on the bell crank lever 15 by means of the resilient pin 14. The spring 11 is now fully biased. This position is shown in FIG. 2.

In order to activate the primed condition automatically as the patient breathes in actively during the inhaling phase, a spring-loaded valve 17 and a bent lever mechanism 18 are provided. As seen from FIG. 1, valve 17 extends at right angles to the air stream in the air space or chamber 99. As the patient inhales through the mouthpiece 16 an low pressure is produced in front of the valve 17, causing the latter to pivot upwards and thus release the push button 6 by means of the bent lever mechanism 18 and the bell crank lever 15. Bell crank lever 15, valve 17, and bent lever mechanism 18 comprise switching means which respond to the low pressure in the air space of the mouthpiece during active breathing in and automatically trigger the drive of the abrasion device. This push button is moved back into the starting position shown in FIG. 1 by the biased spring 11, whilst the screw thread on the spindle 7 and the pushing member 12 on the push button 6 bring about rotation of the spindle 7. The friction drive-wheel 9 is pressed against the brush friction wheel 10 by the plate spring 8, so that the brush also rotates and thereby brushes powder off the tablet 4 in the desired dosage.

After the valve 17 has opened, the inhalation process causes air to flow through the air inlet slots 20 on the base 19 of the housing, transporting the abraded particles through the air chamber 99 to the mouthpiece 16.

After the end of the inhalation process the protective cap (not shown) is put on. As it is put on, the tablet holder 1 is pressed onto the base 19 of the device and the tablet 3 is moved away from the brush 5. This relieves the stress on the bristles.

After the removal of the protective cap, the flange-like part of the tablet holder 1 simultaneously serves as an indicator of the tablet consumption, as its position varies according to the amount of tablet used up.

The embodiment of the propellent-free inhalation device according to the invention illustrated in FIGS. 1 (and 2) may be modified in numerous ways in terms of its assemblies and components.

Thus, the friction drive-wheel 9 which can be separated from the brush wheel 10 in conjunction with the plate spring 8 may be replaced by a locking pawl mechanism which disengages the spindle 7 and the brush wheel 10 when the spring is put under tension. A locking pawl mechanism of this kind is shown in section in FIG. 3. It has a divided drive pinion 7b which engages in driving mode with depressions in the brush carrier 9a. The connection can be broken by disengagement of the drive pinion.

The brush with radial bristles and a horizontal shaft shown in FIG. 1 may also be replaced by a cup-shaped brush with a vertical shaft, which may be driven by a rack connected to the push button 6.

The mechanism with the valve 17 and bent lever mechanism 18 which cause automatic actuation of the primed state when the patient actively breathes in may be replaced, for example, by a trigger-piston arrangement which responds to low pressure.

Moreover, the air inlet slots 20 need not necessarily be provided on the base of the housing but may also be arranged on the side of the housing 24. Conveniently, corresponding air guidance paths are created in the interior of the housing to ensure that the abraded particles are all conveyed to the mouthpiece 16, if possible without the use of guide walls.

The unit consisting of tablet 4, tablet holder 1, tablet recess 21, compression spring 2 and screw base 22 can be unscrewed from the device and replaced by a new unit. The tablet guide 23 may optionally be included in the replaceable unit, as may the spindle 13 and the stop 3.

It is also possible to replace just the tablet 4.

Moreover, the mouthpiece 16 need not be arranged at the top of the housing 24. It is equally possible to provide the mouthpiece on the side, or level with the brush 5.

We claim:

1. A propellant free inhalation device for use with a solid tablet of a medicinal substance, comprising:
   a housing;
   a holder for containing the tablet;
   a manually operated means for dispensing and metering a dose from the tablet for inhalation by a user, said means for dispensing and metering the dose comprising a shaft and a brush having means for mechanically abrading the tablet, said means for mechanically abrading the tablet including a plurality of bristles, said bristles, responsive to manual operation of said dispensing and metering means by a user, mechanically abrading the tablet and generating the dose for inhalation;
   an air chamber within said housing, said air chamber receiving the dose upon manual operation of said dispensing and metering means by a user; and
   a mouthpiece adapted to be engaged by a user's mouth wherein inhalation by a user through said mouthpiece causes air to flow through said air chamber and to entrain the dose.

2. A propellant free inhalation device according to claim 1, further comprising:
   a spring biased against said holder; and
   means for limiting the dose to a predetermined amount comprising an adjustable stop, wherein said adjustable stop limits the movement of said holder responsive to said spring biased against said holder.

3. A propellant free inhalation device according to claim 2, further comprising:
   a drive mechanism connected to said means for dispensing and metering, and means for manually tensioning said drive mechanism, said manual tensioning means comprising a push button.

4. A propellant free inhalation device according to claim 1, further comprising:
   a drive mechanism connected to said means for dispensing and metering, and means for manually tensioning said drive mechanism, said manual tensioning means comprising a push button.

5. A propellant free inhalation device according to claim 4, further comprising:
   switching means for automatically triggering said drive mechanism disposed within said housing and responsive to low pressure in said air chamber generated by user inhalation.

6. A propellant free inhalation device according to claim 5, wherein said switching means comprises:

a spring-loaded valve which extends at right angles to the air stream in said air chamber;

a bent lever mechanism connected to said spring-loaded valve; and a disengaging device for said drive mechanism operatively connected to said bent lever mechanism.

7. A propellant free inhalation device according to claim 6, wherein said drive mechanism comprises:

a spindle having first and second ends, said first end connected to said push button, and said second end connected to said housing;

a drive spring surrounding said spindle, said drive spring being tensioned responsive to translatory movement of said spindle; and a drive-wheel mounted on said spindle, said drive wheel being separated from said abrasion device responsive to tensioning of said drive spring.

8. A propellant free inhalation device according to claim 4, wherein said drive mechanism comprises:

a spindle having first and second ends, said first end connected to said push button, and said second end connected to said housing;

a drive spring surrounding said spindle, said drive spring being tensioned responsive to translatory movement of said spindle; and a drive-wheel mounted on said spindle, said drive wheel being separated from said abrasion device responsive to tensioning of said drive spring.

9. A propellant free inhalation device according to claim 8, further comprising:

a brush friction wheel operatively connected to said drive wheel, said drive wheel being released from said brush friction wheel responsive to translatory movement of said spindle against said drive spring.

10. A propellant free inhalation device according to claim 8: wherein said drive wheel comprises a pinion operatively connected in driving mode to said abrasion device, said drive wheel being released from said abrasion device responsive to translatory movement of said spindle against said drive spring.

11. A propellant free inhalation device according to claim 5, wherein said switching means comprises:

a trigger-piston which actuates in response to low pressure.

12. A propellant free inhalation device according to claim 5, wherein said drive mechanism comprises:

a spindle having first and second ends, said first end connected to said push button, and said second end connected to said housing;

a drive spring surrounding said spindle, said drive spring being tensioned responsive to translatory movement of said spindle; and a drive-wheel mounted on said spindle, said drive wheel being separated from said abrasion device responsive to tensioning of said drive spring.

13. A propellant free inhalation device according to claim 12, further comprising:

a brush friction wheel operatively connected to said drive wheel, said drive wheel being released from said brush friction wheel responsive to translatory movement of said spindle against said drive spring.

14. A propellant free inhalation device according to claim 12, wherein said drive wheel comprises a pinion operatively connected in driving mode to said abrasion device, said drive wheel being released from said abrasion device responsive to translatory movement of said spindle against said drive spring.

15. A propellant free inhalation device according to claim 1, wherein said abrasion device is separable from the solidified medicinal substance.

16. A propellant free inhalation device according to claim 1, wherein said holder is configured to contain solidified medicinal substance in the form of a square tablet.

17. A propellant free inhalation device according to claim 1, wherein said bristles are disposed radially about said shaft.

18. A propellant free inhalation device according to claim 17, wherein said shaft is horizontally disposed.

19. A propellant free inhalation device according to claim 1, wherein said brush is cup-shaped and said shaft is vertically disposed.

* * * * *